(12) United States Patent
Woehr

(10) Patent No.: US 9,867,951 B2
(45) Date of Patent: Jan. 16, 2018

(54) HINGED CAP NEEDLE ASSEMBLIES AND RELATED METHODS

(71) Applicant: B. BRAUN MELSUNGEN AG, Melsungen (DE)

(72) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 464 days.

(21) Appl. No.: 14/248,004

(22) Filed: Apr. 8, 2014

(65) Prior Publication Data

US 2015/0283332 A1  Oct. 8, 2015

(51) Int. Cl.

| B65D 85/24 | (2006.01) |
| A61M 5/32 | (2006.01) |
| A61M 5/00 | (2006.01) |
| B65B 7/28 | (2006.01) |
| B65D 83/02 | (2006.01) |

(52) U.S. Cl.
CPC .......... *A61M 5/3216* (2013.01); *A61M 5/002* (2013.01); *A61M 5/3202* (2013.01); *B65B 7/28* (2013.01); *B65D 83/02* (2013.01); *A61M 2005/3206* (2013.01); *A61M 2005/3217* (2013.01); *A61M 2207/00* (2013.01)

(58) Field of Classification Search
CPC .......... A61B 17/06114; A61B 19/0262; A61B 50/3001; A61M 5/3202; A61M 19/0262; B65D 85/24
USPC ........ 206/365, 364, 363, 380; 604/192, 263, 604/110
See application file for complete search history.

(56) References Cited

U.S. PATENT DOCUMENTS

| 3,074,540 | A | * | 1/1963 | Beich .................... A61M 5/002 206/366 |
| 4,659,330 | A | | 4/1987 | Nelson et al. |
| 4,664,259 | A | | 5/1987 | Landis |
| 4,982,842 | A | | 1/1991 | Hollister |
| 5,139,489 | A | | 8/1992 | Hollister |
| 5,154,285 | A | | 10/1992 | Hollister |
| 5,188,611 | A | | 2/1993 | Orgain |
| 5,232,454 | A | | 8/1993 | Hollister |

(Continued)

FOREIGN PATENT DOCUMENTS

| EP | 0916355 | 5/1999 |
| WO | WO 2009/007718 | 1/2009 |
| WO | WO 2013/029529 | 3/2013 |

OTHER PUBLICATIONS

International Search Report on related PCT application (PCT/EP2015/057638) from International Searching Authority (EPO) dated Oct. 15, 2015.

(Continued)

*Primary Examiner* — King M Chu
(74) *Attorney, Agent, or Firm* — Klein, O'Neill & Singh, LLP

(57) ABSTRACT

A dual purpose needle assembly and related method are disclosed having a needle hub and needle sealed inside a packaging housing with a film cover or layer. The packaging housing has separately formed and subsequently joined cap and base unit with a living hinge optionally joining the two components. The needle assembly is usable without additional packaging and is usable as a hinged cap safety device upon removal of at least a section of the film cover.

28 Claims, 11 Drawing Sheets

(56) References Cited

U.S. PATENT DOCUMENTS

| | | |
|---|---|---|
| 5,232,455 A | 8/1993 | Hollister |
| 5,277,311 A | 1/1994 | Hollister |
| 5,312,368 A | 5/1994 | Haynes |
| 5,423,765 A | 6/1995 | Hollister |
| 5,486,163 A | 1/1996 | Haynes |
| 5,490,841 A | 2/1996 | Landis |
| 5,509,907 A | 4/1996 | Bevilacqua |
| 5,584,816 A | 12/1996 | Gyure et al. |
| 5,599,313 A | 2/1997 | Gyure et al. |
| 5,599,318 A | 2/1997 | Sweeney et al. |
| 5,603,699 A | 2/1997 | Shine |
| 5,632,732 A | 5/1997 | Szabo et al. |
| 5,643,219 A | 7/1997 | Burns |
| 5,662,617 A | 9/1997 | Odell et al. |
| 5,669,889 A | 9/1997 | Gyure et al. |
| 5,681,295 A | 10/1997 | Gyure et al. |
| 5,693,022 A | 12/1997 | Haynes |
| 5,704,920 A | 1/1998 | Gyure |
| 5,733,265 A | 3/1998 | Bachman et al. |
| 5,746,726 A | 5/1998 | Sweeney et al. |
| 5,807,351 A | 9/1998 | Kashmer |
| 5,810,775 A | 9/1998 | Shaw |
| 5,823,997 A | 10/1998 | Thorne |
| 5,836,920 A | 11/1998 | Robertson |
| 5,868,716 A | 2/1999 | Sweeney et al. |
| 5,885,249 A | 3/1999 | Irisawa |
| 5,891,103 A | 4/1999 | Burns |
| 5,913,846 A | 6/1999 | Szabo |
| 5,919,165 A | 7/1999 | Benson |
| 5,957,892 A | 9/1999 | Thorne |
| 5,980,488 A | 11/1999 | Thorne |
| 6,042,570 A | 3/2000 | Bell et al. |
| 6,096,024 A | 8/2000 | Graves et al. |
| 6,149,629 A | 11/2000 | Wilson et al. |
| RE37,110 E | 3/2001 | Hollister |
| RE37,252 E | 7/2001 | Hollister |
| 6,254,575 B1 | 7/2001 | Thorne |
| 6,280,420 B1 | 8/2001 | Ferguson et al. |
| 6,298,541 B1 | 10/2001 | Newby et al. |
| 6,319,232 B1 | 11/2001 | Kashmer |
| 6,328,713 B1 | 12/2001 | Hollister |
| 6,334,857 B1 | 1/2002 | Hollister et al. |
| 6,355,021 B1 | 3/2002 | Nielsen et al. |
| 6,436,086 B1 | 8/2002 | Newby et al. |
| 6,440,104 B1 | 8/2002 | Newby et al. |
| 6,517,522 B1 | 2/2003 | Bell et al. |
| 6,551,287 B2 | 4/2003 | Hollister et al. |
| 6,582,397 B2 | 6/2003 | Alesi et al. |
| 6,592,556 B1 | 7/2003 | Thorne |
| 6,616,638 B2 | 9/2003 | Peters, III |
| 6,635,032 B2 | 10/2003 | Ward |
| 6,648,855 B2 | 11/2003 | Crawford et al. |
| 6,699,217 B2 | 3/2004 | Bennett et al. |
| 6,719,737 B2 | 4/2004 | Kobayashi |
| 6,752,788 B2 | 6/2004 | Tuen |
| 6,780,169 B2 | 8/2004 | Crawford |
| 6,811,547 B2 | 11/2004 | Wilkinson |
| 6,824,531 B1 | 11/2004 | Zecha et al. |
| 6,840,922 B2 | 1/2005 | Nielsen et al. |
| 6,869,418 B2 | 3/2005 | Marano-Ford |
| D505,200 S | 5/2005 | Simpson et al. |
| 6,918,891 B2 | 7/2005 | Bressler et al. |
| 6,921,388 B2 | 7/2005 | Swenson |
| 6,951,551 B2 | 10/2005 | Hudon |
| RE39,107 E | 5/2006 | Shaw |
| 7,128,726 B2 | 10/2006 | Crawford et al. |
| 7,147,623 B2 | 12/2006 | Mathiasen |
| 7,156,825 B2 | 1/2007 | Hudon |
| 7,163,526 B2 | 1/2007 | Leong et al. |
| 7,186,240 B1 | 3/2007 | Kronja |
| 7,198,618 B2 | 4/2007 | Ferguson et al. |
| 7,201,736 B2 | 4/2007 | Hauri |
| 7,217,258 B2 | 5/2007 | Caizza |
| 7,220,249 B2 | 5/2007 | Hwang et al. |
| 7,223,258 B2 | 5/2007 | Crawford |
| 7,250,038 B2 | 7/2007 | Simpson et al. |
| 7,322,963 B2 | 1/2008 | Goh |
| 7,387,615 B2 | 6/2008 | Coelho et al. |
| 7,413,560 B2 | 8/2008 | Chong et al. |
| 7,488,306 B2 | 2/2009 | Nguyen |
| 7,537,581 B2 | 5/2009 | Hwang |
| 7,553,296 B2 | 6/2009 | Bedford et al. |
| 7,591,800 B2 | 9/2009 | Nguyen |
| 7,635,352 B2 | 12/2009 | Adams |
| 7,648,480 B2 | 1/2010 | Bosel et al. |
| 7,833,198 B2 | 11/2010 | Bressler et al. |
| 7,854,723 B2 | 12/2010 | Hwang et al. |
| 7,967,794 B2 | 6/2011 | Bosel et al. |
| 8,016,796 B2 | 9/2011 | Simas, Jr. et al. |
| 8,029,463 B2 | 10/2011 | Hauri |
| 8,038,654 B2 | 10/2011 | Lim et al. |
| 8,057,431 B2 | 11/2011 | Woehr et al. |
| 8,167,851 B2 | 5/2012 | Sen |
| 8,182,451 B2 | 5/2012 | Bressler et al. |
| 8,226,576 B2 | 7/2012 | Swenson et al. |
| 8,226,617 B2 | 7/2012 | Ferguson et al. |
| 8,251,961 B2 | 8/2012 | Hauri |
| 8,277,408 B2 | 10/2012 | Crawford et al. |
| 8,425,472 B2 | 4/2013 | Bressler et al. |
| 2002/0062107 A1 | 5/2002 | Parmigiani et al. |
| 2002/0072715 A1 | 6/2002 | Newby et al. |
| 2003/0036732 A1* | 2/2003 | Marano-Ford ...... A61M 5/3216 604/199 |
| 2003/0125676 A1 | 7/2003 | Swenson et al. |
| 2003/0181860 A1 | 9/2003 | Swenson |
| 2003/0181868 A1 | 9/2003 | Swenson |
| 2003/0187398 A1 | 10/2003 | Crawford |
| 2003/0187399 A1 | 10/2003 | Crawford |
| 2003/0220618 A1 | 11/2003 | Crawford |
| 2005/0004531 A1 | 1/2005 | Hwang et al. |
| 2005/0124944 A1 | 6/2005 | Hwang |
| 2005/0146081 A1 | 7/2005 | MacLean et al. |
| 2005/0269227 A1* | 12/2005 | Erickson ............. A61M 5/3205 206/366 |
| 2006/0124643 A1 | 6/2006 | Markert et al. |
| 2006/0149188 A1 | 7/2006 | Simas, Jr. |
| 2006/0200078 A1 | 9/2006 | Konrad |
| 2006/0270947 A1 | 11/2006 | Crawford et al. |
| 2007/0088261 A1 | 4/2007 | Lew et al. |

OTHER PUBLICATIONS

Written Opinion on related PCT application (PCT/EP2015/057638) from International Searching Authority (EPO) dated Oct. 15, 2015.
Written Opinion on related SG application (11201607773T) from the International Property Office of Singapore (IPOS) dated Aug. 30, 2017.

* cited by examiner

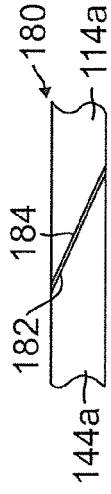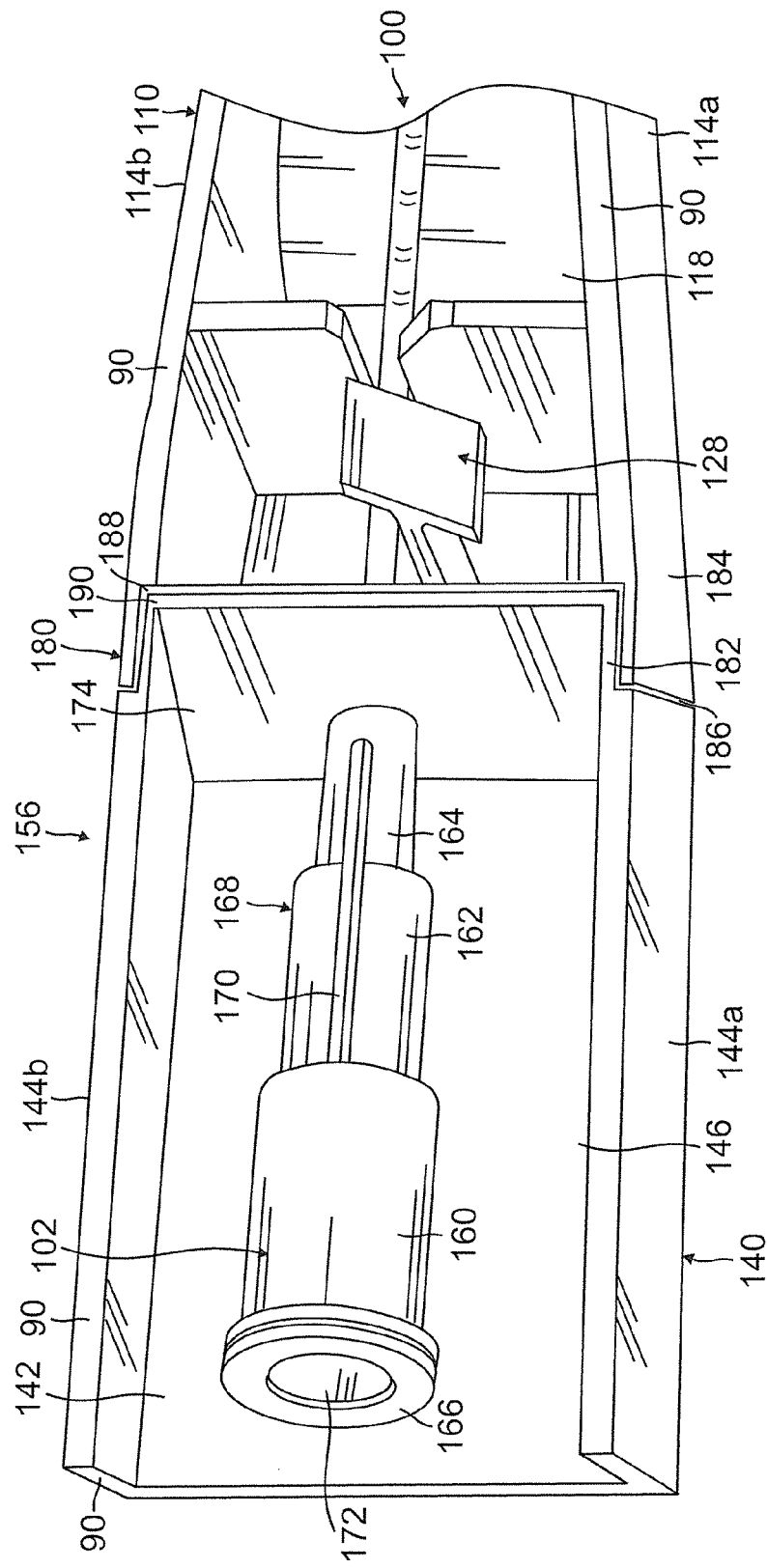

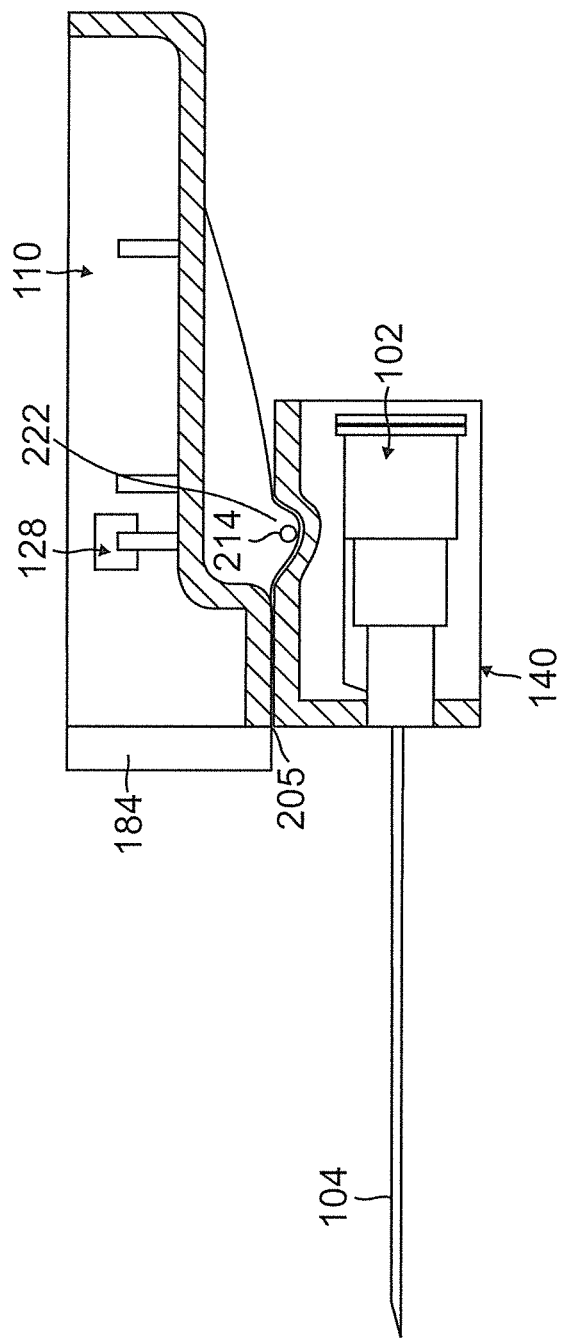

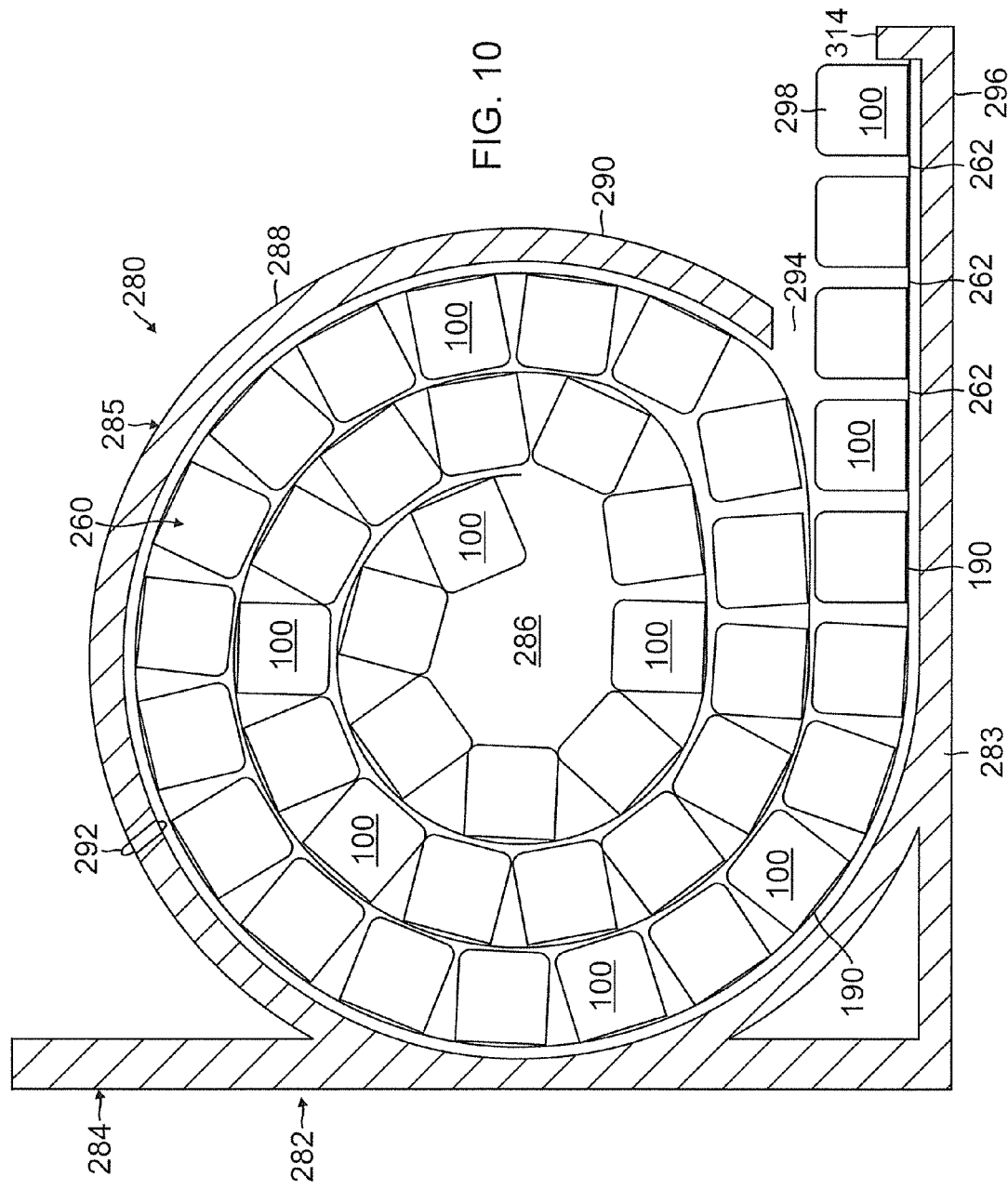

HINGED CAP NEEDLE ASSEMBLIES AND RELATED METHODS

FIELD OF ART

The present invention generally relates to safety needle assemblies and more specifically to hinged cap needle assemblies with packaging and related methods.

BACKGROUND

Hinged cap needle assemblies are well known and are designed to cap a needle following use to prevent inadvertent needle sticks. The combination needle hub and needle is typically used with a syringe. The hinged cap may engage the needle hub via a collar to convert the standard needle hub into a hinged cap safety needle device. The needle hub and needle may instead be incorporated with the cap via a hinge in a unitary or integrated construction.

An embodiment of a prior art hinged cap device comes with a removable temporary cap mounted over the needle in a packaging unit, which differs from the hinged cap for capping needle following use. This has the disadvantage that the hinged cap must be set off at an angle from the removeable cap and thus increases the size of the package. This in turn has negative consequences for the whole distribution chain. After the hinged cap device is removed from the packaging unit, the hub of the hinged cap is placed onto a syringe tip and the temporary cap removed and discarded. The needle is then used, such as to draw a sample or deliver an injection, and then subsequently capped with the hinged cap, which has means for preventing re-opening of the cap to deter re-use.

Recapping is a common procedure for periods between drawing up fluids into a syringe and administering injections through the needle. The recapping procedure can occasionally cause needle sticks since users sometime misalign the needles with the openings on the caps. Injuries can also occur after an injection and prior to the discarding of the needles. Needle sticks can be painful, but can also cause great inconvenience because all needle sticks must be reported. Also, since needles related to needle sticks must be discarded, medications contained within the syringes are unnecessarily wasted. Furthermore, fluids linked to these "clean" type of needle sticks can cause injuries and adverse reactions.

SUMMARY

A combination safety needle assembly and a packaging system for the safety needle assembly is provided in accordance with aspects of the present disclosure. The combination device comprising: a base unit comprising a base wall located between two sidewalls and defining an interior cavity; a cap connected to the base unit at an interface, the cap comprising a base wall located between two sidewalls and defining an interior cavity having a latch; a needle hub and a needle combination, said needle hub attached to the base unit and said needle extending into the interior cavity of the cap; wherein the sidewalls of the cap and the sidewalls of the base unit define an open perimeter edge and the interior cavity of the cap and the interior cavity of the base unit define a package cavity; and wherein a thermoplastic film is attached to the open perimeter and extend across the interface between the cap and the base unit to enclose the combination needle hub and needle within the package cavity and forms a hinge at the interface.

The combination wherein the thermoplastic film can comprise a first film piece and a second film piece separated from one another by a perforation or a distinct separation.

The combination wherein the two sidewalls of the base unit and the two sidewalls of the cap can overlap along an axial direction.

The combination wherein the needle hub can be unitarily formed with the base unit.

The combination wherein the needle hub can be molded with a distal wall on the base unit.

The combination wherein the distal wall on the base unit can connect to the base wall and the two sidewalls of the base unit.

The combination can further comprise a latch comprising a post and a ramp mounted at an end of the post. The needle can be located on a first side of the latch in a holding state and on a second side of the latch in a locked state.

A further feature of the present disclosure is a combination safety needle assembly and a packaging system for the safety needle assembly comprising a unique hinge system. The combination device comprising a base unit comprising an enclosure having a base wall located between two sidewalls, said enclosure having an interior cavity and a perimeter edge with a proximal end edge; a cap hingedly connected to the base unit at an interface by a film layer, the cap comprising an enclosure having a base wall located between two sidewalls, said enclosure defining an interior cavity having a latch and a perimeter edge; a needle hub and a needle combination, said needle hub attached to the base unit and said needle extending into the interior cavity of the cap; wherein the needle hub is recessed within the proximal end edge of the base unit and wherein a film cover is attached to the perimeter edge of the cap and the perimeter edge of the base unit to enclose the combination needle hub and needle within the interior cavity of the cap and the interior cavity of the base unit.

The combination wherein the film layer and the film cover can be spaced from one another.

The combination wherein a perforation can be provided between the film layer and the film cover.

The combination wherein the two sidewalls of the cap and the two sidewalls of the base unit can overlap along an axial direction.

The combination can further comprise a needle assembly connected to the base unit and cap via a tear line in an array.

The combination wherein the needle hub can be unitarily formed with the base unit.

The combination wherein the needle hub can snap fit into a C-clamp formed on the base unit.

A dual use needle assembly comprising a packaging housing having a needle hub and a needle located within an enclosure having a perimeter edge and a film cover attached to the perimeter edge to seal the needle hub and needle within the packaging housing, and wherein the packaging housing comprises a cap having two sidewalls and a base unit having two sidewalls and wherein the sidewalls of the cap and the base unit overlap along an axial direction.

The dual use needle assembly wherein the cap can attach to the base unit by a living hinge.

The dual use needle assembly wherein the cap can attach to the base unit by a second film cover that spans across a seam located between the cap and the base unit.

The dual use needle assembly can further comprise a second dual use needle assembly and a third dual use needle assembly connected in an array.

A further feature of the present disclosure is a method for manufacturing a dual use needle assembly. The method comprising forming a base unit comprising two sidewalls, a base wall, and a needle hub having a needle with a sharpened needle tip; forming a cap comprising two sidewalls and a base wall; attaching a film cover to outer edges of the two sidewalls of the cap and of the base unit; and overlapping the two sidewalls of the cap with the two sidewalls of the base unit along an axial direction.

The method can further comprise attaching a second film cover across a seam located between the base wall of the cap and the base wall of the base unit.

The method wherein the base wall of the base unit can attach to the base wall of the cap by a living hinge.

The method can further comprise placing the needle on a first side of a latch comprising a post and a ramp.

A still yet further feature of the present disclosure is a dispenser system comprising a dispenser having a wall structure defining a storage space, an array of needle assemblies, a dispersed bundle of needle assemblies, or both an array of needle assemblies and a dispersed bundle of needle assemblies located in the storage space; and wherein each needle assembly comprises: a package housing comprising a base unit comprising sidewalls and a base wall hingedly connected to a cap comprising sidewalls and a base wall; a film cover affixed to a perimeter edge of the package housing; and a needle hub and needle sealed inside the package housing by the film cover; and sidewalls of the cap and the base unit overlapping along an axial direction.

The dispenser system wherein the dispenser has a frame for mounting on a wall or place on a flat surface.

BRIEF DESCRIPTION OF THE DRAWINGS

These and other features and advantages of the present device, system, and method will become appreciated as the same becomes better understood with reference to the specification, claims and appended drawings wherein:

FIG. 2 is an expanded perspective view of a section of the needle assembly of FIG. 1.

FIG. 2A is a partial top view of an alternative isolation zone.

FIG. 4 is a cross-sectional side view of the needle assembly of FIG. 1 in a cap retracted and needle exposed position.

FIG. 10 shows a dispenser system in accordance with aspects of the present disclosure for dispensing needle assemblies.

DETAILED DESCRIPTION

The detailed description set forth below in connection with the appended drawings is intended as a description of the presently preferred embodiments of hinged cap needles provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
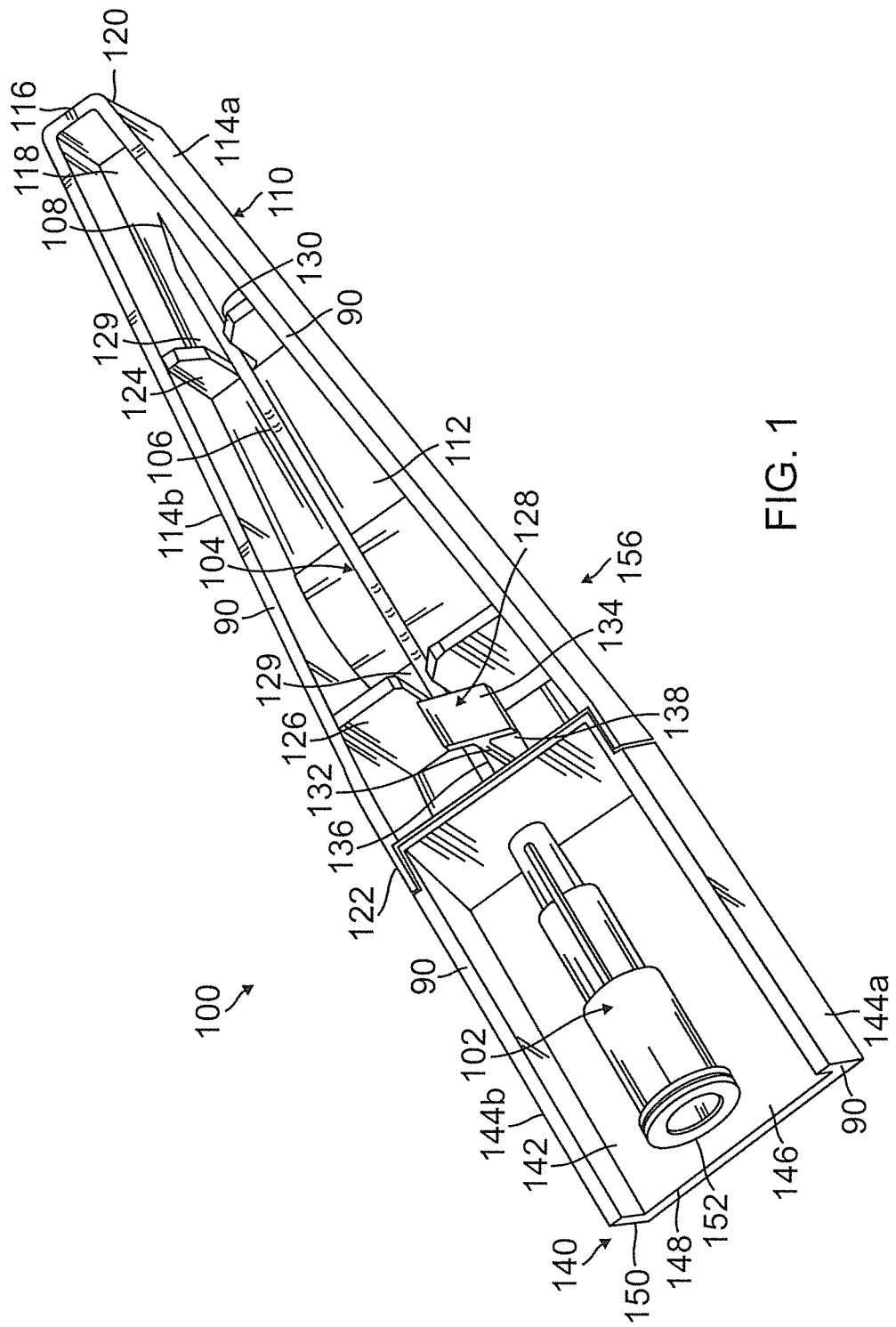
FIG. 1 is a schematic perspective view of a needle assembly provided in accordance with aspects of the present device, system, and method.

With reference now to FIG. 1, a perspective view of needle assembly 100 provided in accordance with aspects of the present embodiment is shown. The needle assembly 100 may sometime be referred to as a hinged cap needle assembly or simply hinged cap device or assembly. As shown, the needle assembly 100 comprises a needle hub 102 having a needle 104 attached thereto. The needle 104 comprising a needle shaft 106 defining a lengthwise axis and a sharpened distal tip 108. Thus, as used herein, the term "axial" implies a spatial relationship along the axial length or axial direction of the needle axis. The needle assembly 100 is shown in a covered positioned in which the needle 104 is positioned inside a cap 110 and the needle tip 108 is covered by the wall enclosures of the cap to prevent inadvertent needle sticks.

As shown, the cap 110 has a base wall 112 disposed between two sidewalls 114a, 114b and an end wall 116, which together define an interior cavity 118, such as an interior space, for accommodating or receiving the needle 104. The cap 110 has a distal end 120 and a proximal end 122. The two sidewalls 114a, 114b may be generally parallel so that the width of the cap and the proximal and distal ends 120, 122 are about the same width. As shown, the sidewalls 114a, 114b tapered inwardly in the direction of the needle shaft 106 so that the distal end 120 of the cap 110 is narrower than the proximal end 122 of the cap. Conceivably the distal end 120 can be wider than the proximal end 122.

Internally of the interior cavity 118, a first rib set 124, a second rib set 126, and a latch 128 are provided. The first and second rib sets 124, 126 are attached to the base wall 112 and the sidewalls 114a, 114b to structurally support the walls and each comprises a passage 129 for receiving the needle shaft 106. The ribs preferably include a tapered inlet end 130 to facilitate centering the shaft in the event of a misalignment or contact into the two passages 129 when closing the cap over the needle.

The latch 128 is shown with a leg or post 132 and a ramp 134 connected to the post or leg. As shown, the ramp 134 is slanted and is bisected by the leg. The slanted configuration of the ramp defines a first side 136 in which the wall and leg define an obtuse angle therebetween and a second side 138 in which the wall and the leg define an acute angle therebetween. As shown, the needle 104 is located on the first side 136 of the latch 128 when the cap is rotated to cover the needle in the packaged position or pre-use configuration. After using the needle, the cap 110 can be rotated and the needle 104 moved to the second side 138 of the latch 128 to lock the needle within the cap 110. Thus, the latch 128 is understood to have a hold side and a lock side, which can be the first side 136 and the second side 138, respectively.

Also shown is a base unit 140 surrounding the needle hub 102. In one exemplary embodiment, the base unit 140 has a base wall 142 located between two sidewalls 144a, 144b, which together define a cavity 146 for accommodating the needle hub 102. The cavity 118 of the cap and the cavity 146 of the base unit together define a package cavity. Sufficient clearance is provided around the needle hub 102 for attaching a standardized luer lock syringe. As further discussed below, the cap 110 and the base unit 140 are separately formed, such as by plastic molded injection, and subsequently attached together using a unique hinge system of the present device, system, and method. The base unit 140 and the cap 110 has a lengthwise axis, which is generally coincident with the lengthwise axis of the needle.

In one example, the proximal end edge 148 of the base wall 142, the proximal end edge 150 of the sidewalls 144a, 144b both extend further proximally of the proximal end edge 152 of the needle hub. In other words as shown, the base unit 140 has at least one or more walls having an end edge that extend further proximally, i.e., the needle hub is recessed from the end edge of one or more walls, of the needle hub so as to cover the needle hub. Alternatively, the proximal end edges of the base and side walls can be flush with the proximal end edge of the needle hub. As further discussed below, the base unit 140 with the extended walls and the cap 110 define a package or packaging housing 156 to house the needle hub 102 and needle 104 and also functions as a safety shield for capping the needle tip 108 following use. A separate package or blister pack shell for housing the needle assembly 100 during manufacturing, shipping, and storage is not required with the present needle assembly, which has a self-contained packaging system, as further discussed below. The open perimeter edge 90 of the base unit 140 and the cap 110 together define a perimeter for a film cover to seal in the two respective cavity sections 118, 146 with the needle and needle hub located inside, as further discussed below. The film cover allows the needle assembly 100 to be manufactured and shipped without separately providing a package or blister pack. Thus, an aspect of the present device, system, and method is a dual use needle assembly 100 that is configured to house a needle hub 102 and needle 104 for storing, shipping, and distribution purposes and that also functions as a safety cap for capping the needle following use.

With reference now to FIG. 2, an expanded perspective view of the needle assembly 100 of FIG. 1. As shown, the needle hub 102 comprises a base hub section 160 having standardized exterior threads 166 and a nose section 168 having the needle 104 attached thereto. The hub 102 has an interior bore 172 that is sized with a standardized female Luer taper and together with the threads 166 define a standardized threaded female Luer for receiving a standardized male Luer, with (Luer lock) or without (Luer slip) a threaded collar. As shown, the nose section 168 comprises a first nose section 162 and a second nose section 164. The first nose section 162 can have a larger diameter than the second nose section 164 but smaller than the base hub section 160. In an alternative embodiment, the nose section 168 has a single constant diameter or a single tapering surface, such as a cone surface. An optional rib 170 is provided connecting to both the base hub section 160 and the nose section 168. In an example, the needle hub 102 is attached to the base wall 142 of the base unit 140. For example, the needle hub 102 may be unitarily formed, via plastic injection molding, to the base wall 142. A rib or connecting channel may be formed during plastic injection molding between the needle hub nose section and the base wall. Alternatively, two ribs may be provided to connect the needle hub to the two sidewalls of the base unit. The rib or ribs should be located sufficiently distal of the threads 166 so as not to interfere with a threaded collar of a male Luer during use of the needle assembly. Also, the needle hub 102 should be sufficiently spaced from the base wall 142 and the two sidewalls 144a, 144b to permit connection with a male threaded Luer, such as a syringe tip, without interfering with the collar of the male threaded Luer. In the present embodiment, the needle hub 102 is attached to a distal wall 174 of the base unit 140. For example, the nose section 168, such as the second nose section 164, is unitarily formed with the distal wall 174. The needle hub is therefore suspended within the base unit at its nose section. In another embodiment, at least one rib is provided between the needle hub and one of the walls, either the base wall or one of the two sidewalls, in addition to the connection with the distal wall 174. Thus, in one embodiment, the base unit 140 and the needle hub 102 are understood to be formed as a unitary construction, such as by injection molding the two as a single unit. In yet another embodiment, a C-clamp type structure is molded with the base unit 140 and the needle hub 102 engages, such as snaps into, the C-clamp type structure. Adhesive or welding may be used to provide a more secured arrangement when incorporating the C-clamp type structure.

As noted above, the dual use needle assembly 100 is configured for use as a packaging device with a needle and needle hub inside and as a needle safety device with a protective hinged cap, as further discussed below. To ensure appropriate isolation of the interior cavities for packaging purposes, the present package housing 156 is equipped with an isolation zone 180 between the base unit 140 and the cap 110. In one example, the isolation zone 180 comprises matching contoured sidewall sections 182, 184 that mate to form a tight fitting section having a form fit with a gap 186 therebetween, which is shown enlarged for discussion purposes only. The surfaces where the two cut sidewall sections 182, 184 mate can physically contact so as to eliminate any path for potential contamination and/or bio growth. As shown, the two sidewalls 144a, 144b of the base unit 140 have part of their wall layers reduced or stepped to mate with corresponding stepped sections formed on the two sidewalls 114a, 114b of the cap 110. To facilitate closing the cap 110 over the needle and the cut sidewall sections 182, 184 mesh when closed, the mated corners 188, 190 may be relieved or beveled. In an alternative embodiment, the isolation zone 180 may be provided with a different cut configuration. As shown in the alternative embodiment of FIG. 2A, the isolation zone 180 can utilize two single cuts, such as two matching tapered surfaces, on each of the two mating sidewalls 114a/144a and 114b/144b to provide the tight fitting contacts.

Figure 3:
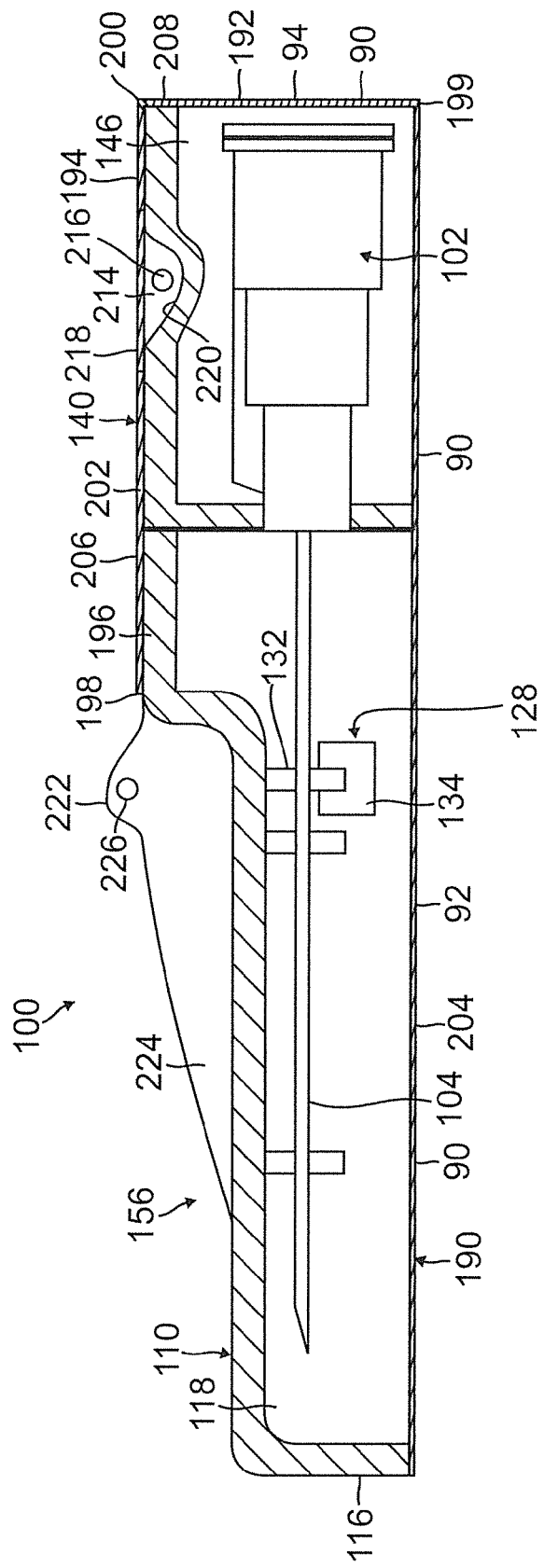
FIG. 3 is a cross-sectional side view of the needle assembly of FIG. 1 with a film layer covering the housing cavities.

FIG. 3 is a cross-sectional side view of the needle assembly 100 of FIG. 1 in a sealed or packaged state. A film cover or layer 190 is shown applied to the open perimeter edge 90 of the package housing 156 to seal the interior cavity sections 118, 146 of the housing to thereby seal the needle hub 102 and needle. As shown, the film cover 190 is bonded to the perimeter edge 90 from the end wall 116, to end edge 192 of the base unit 140, and over the rear exterior surface 194 of the base unit and the rear exterior surface 196 of the cap 110. An extended piece or extension may be provided beyond the end wall 116 to serve as a gripping point or section to facilitate gripping and removing the film cover 190, which may be considered a film cover layer. If the film cover 190 is wider than the distal end of the cap 110, which in the present embodiment has a tapered distal end, then there will be a pull tab on either side of the two sidewalls 114a, 114b to facilitate opening of the package. In one example, the film cover 190 is a single continuous piece that extends from the end wall 116 of the cap to the terminal end 198, at the rear exterior surface 196 of the cap 110. In another example, the film cover 190 is formed from two or more separate strips or pieces. For example, the first film piece 204 can extend from the end wall 116 to the first base corner 199 and around the first base corner to the second base corner 200 of the base unit 140. In another example, the first film piece can extend past the second base corner 200. A second film piece 206 can extend between the cap 110 and the base unit 140 and across the interface or seam 202 between the two components. Preferably, a clear separation line or a perforation 208 is provided between the first film piece 204 and the second film piece 206. For example, a clear separation or a perforation can be provided between the first film piece 204 and the second film piece 206 at the base corner 200 of the base unit. When the first film piece 204 is removed from the package housing 156, the second film piece 206 remains and holds the cap 110 to the base unit 140. The second film piece 206 therefore functions as a hinge 205 between the cap 110 and the base unit 140. The hinge 205 enables the cap 110 to rotate back against the base unit 140 and away from the needle 104, as further discussed below.

The film cover 190 is shown affixed to the open perimeter edge 90 along the lengthwise direction 92 of the package housing 156 and along the widthwise direction 94 around the first base corner 199 of the package housing. Preferably, the film cover 190 continues to the second base corner 200 of the base unit 140. Together with the wall surfaces 116, 114a, 114b, 144a, 144b of the package housing 156, the film cover 190 seals in the interior cavities 118, 146 of the package housing 156. The same film cover 190, either as a continuous piece or as a separate film piece, extends along the rear exterior surface 194 of the base unit and the rear exterior surface 196 of the cap and across the interface or seam 202 where the two components are joined. In one embodiment, the film cover 190 has at least three distinct film cover sections: the first extending across the length of the package housing, the second extending across the width of the package housing near the needle hub opening, and the third extending across the rear exterior surfaces of the cap and the base unit and across the seam or interface 202 to also function as a hinge 205. The sealed assembly further comprises at least two overlapping sidewalls. As disclosed, two sets of sidewalls are overlapped at two different isolation zones 180 (FIG. 2), one on each side of the package unit. In still another example, the film cover 190 extends across the length and the width of the package housing but wherein the cap and the base unit are joined by a living hinge, which is a unitarily formed plastic strip that is formed with the cap 110 and the base unit 140.

In one example, the film cover 190 is configured to bond to a variety of rigid plastic package housing material, including polyethylene (PE), polypropylene (PE), polyethylene terephthalate (PET), polyvinyl chloride (PVC), and other equivalent plastic materials. The film cover 190 may be a single film type or a single film sheet, such as HDPE (high density PE). More preferred, the film 190 is a multi-laminate comprising several different film types or layers with an optional metallic foil layer to provide oxygen impermeability. For example, the film cover 190 can comprise an outer layer of metalized PET, adhesive, and a poly film, such as PE. Another example includes a first outer most PET layer, a second or next layer of PE, a third or next layer of foil, and a fourth or most inner layer of PE. Appropriate adhesive is understood to be provided between the layers. Another example includes polyvinylidene chloride (PVDC), adhesive, and poly film, such as PE or HDPE, or PP. Yet another film material could be spun bound polypropylene, such as the Tyvek® brand of films. In some examples, the first film piece 204 differs in material construction from the second film piece 206. For example, the second film piece 206 may be thicker and selected with more durable materials than the first film piece to function as a hinge whereas the first film piece 206 is configured to seal in the interior cavities only and be peelable. The second film piece 206 should resist and should not be easily peeled from the rear exterior surfaces of the cap and the base unit. The material for the second film piece 206 should be selected to have a stronger bond to the package housing 156 to better operate as a hinge and be resistant or impervious to peeling from the wall surfaces of the package housing. In yet other examples, the first and second film pieces are made from the same material but using different sealing applications to possess different bond strengths, such as using different welding temperature, different adhesive, and/or different pressure. It is understood that other film pieces known in the art may be usable with the package housing 156 of the present embodiment in the configuration disclosed.

Also shown in FIG. 3 is a recess 214 formed on the rear exterior surface 194 of the base unit 140, which defines an anchor point. The recess 214 is bounded by a perimeter 218 and a bottom surface 220 and comprises a first detent member 216, which can be a boss or an engagement bore. In one example, the perimeter 218 is generally round. In other examples, the perimeter 218 is oval, irregular in shape, or polygonal, such as square or rectangular. As shown with reference to FIG. 7, the recess 214 is generally rectangular in shape. The film cover layer 190 at the rear exterior surface 194 of the base unit 140 may include an opening formed around the perimeter 218 or may cover the recess 214, such as opening 250 shown in FIG. 7. If the film layer 190 covers the recess 214, a perforation is preferably provided with the film cover or layer 190 at the recess to facilitate tearing or rupturing that section of the film cover or layer to permit accessing the recess 214.

The recess 214 is configured to receive the tab 222 located on the cap 110 when the cap is rotated or retracted away from the needle 104 to expose the needle during use. As shown, the tab 222 projects from an elongated rib 224 formed on the cap 110 and has a second detent member 226 for engaging the first detent member 216 in the recess 214. The second detent member 226 can be the other one of an engagement bore or a boss. The projection defining the tab 222 is sized and shaped to at least partially project into the recess 214 on the base unit 140 to allow the first and second detent members 216, 226 to engage one another to hold the cap 110 in the retracted position, as further discussed below with reference to FIG. 4. In an alternative embodiment, a cap to base unit securing system to maintain the cap in a retracted position may comprise a friction fit and/or an interference fit. For example, the rib 224 on the cap may comprise a blunt edge that slides into a gap provided by two projections formed on the base unit 140 having a gap therebetween. The cap can be held in the retracted position by the friction and/or interference between the blunt edge sliding in between the gap and held by friction and/or interference fit.

With reference again FIG. 3 in addition to FIG. 1, in the sealed state, the cap 110 is firmly secured to the base unit 140 although the two components are separately formed and subsequently joined. As shown and described, the cap 110 and the base unit 140 are secured to one another by the film cover or layer 190. Additionally, the two components are structurally supported laterally of the lengthwise axis of the needle by the shaped contacts 182, 184 at the isolation zone 180. Thus, an aspect of the present disclosure is understood to include a needle assembly 100 comprising a needle hub and needle sealed inside a package housing 156 with a film cover or layer 190, the packaging housing comprising separately formed and subsequently joined cap and base unit. In another example, the cap and the base unit are joined to one another by a living hinge. The needle assembly 100 is usable without additional packaging and is usable as a hinged cap safety device upon removal of at least a section of the film layer 190. In one example, the needle assembly 100 comprises a thermoplastic film that functions as a hinge and wherein the film holds the protective cap to the base unit and wherein the cap is rotatable relative to the base unit about the thermoplastic film and wherein the base unit comprises a needle hub. In the example shown, the needle hub is unitarily formed to the base unit. In another example, the base unit comprises a C-type clamp and the needle hub snap-fit into the C-clamp. Adhesive or welding may be used with the snap-fit configuration to more permanently secure the needle hub to the base unit.

In FIG. 3, an alternative latch 128 comprising a post 132 having a width that is less than the width of the ramp 134 is shown, which differs from the latch of FIG. 1 in which the two widths are the same. In other examples, the post 132 has a width that is wider than the width of the slanted wall. The width and/or thickness at a localized area of the post may be selected to control resiliency or ability of the post to deflect when the slanted wall 134 comes in contact with the needle 104.

With reference now to FIG. 4, the cap 110 is shown pivoted or retracted away from the needle 104 and the tab 222 on the cap engaging the recess 214 on the base unit 140. With reference also to FIGS. 1 and 3 in addition to FIG. 4, the cap 110 may be pivoted by first removing the film cover 190, or at least part of the film cover to leave the remaining film cover bonded to the cap and the base unit to function as a hinge. In an embodiment with a living hinge, the entire film cover 190 may be removed. At this point, the needle 104 is located on the first or hold side 136 of the latch 128 located in the cap 110 (FIG. 1). The obtuse angle between the ramp 134 and the leg 132 allows the needle to slip past the latch 128. For example, the leg 132 and/or the needle 104 can deflect to clear one another to then allow the cap to retract away from the needle. The cap is then pivoted until the first and second detent members 216, 226 engage one another to hold the cap in the retracted position shown in FIG. 4. At this point, the needle hub 102 may be placed over a male Luer tip of a syringe or other medical instrument. Alternatively, the needle hub may be placed over the syringe tip or other medical instrument after removing the film cover layer and before retracting the cap away from the needle. Also shown in FIG. 4 is one of the cut sidewall sections 184 of the cap 110.

Figure 4A:
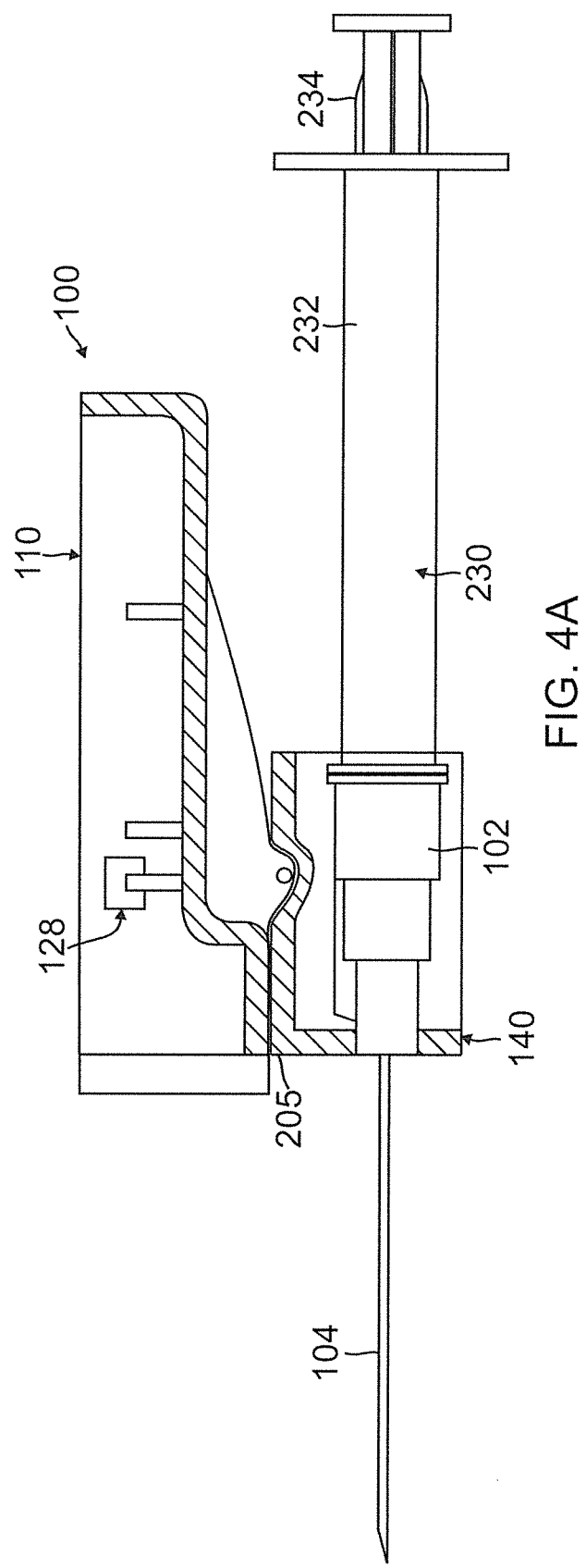
FIG. 4A shows the needle assembly of FIG. 4 coupled to a syringe.

FIG. 4A shows the needle assembly 100 attached to an end of a syringe 230. More specifically, the syringe tip is shown inserted into the bore of the needle hub 102. The syringe 230 is shown with a barrel 232 and a plunger 234 and can embody any prior art syringes. The combination needle assembly 100 and syringe 230 may now be used to draw a sample or provide an injection. Following use, the cap 110 may be pivoted over the needle to cover the needle tip, as further discussed below.

Figure 5:
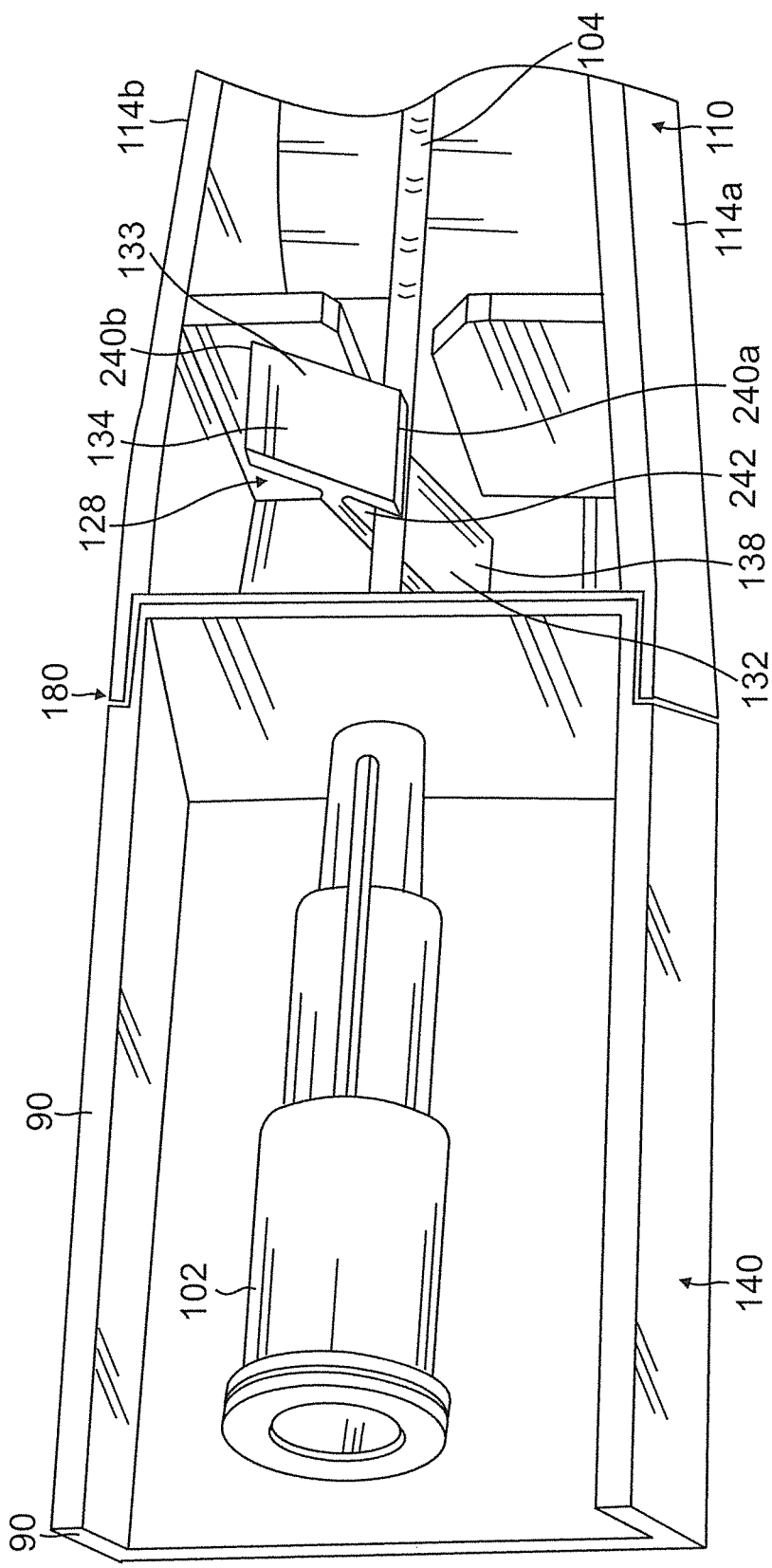
FIG. 5 is an expanded perspective view of a section of the needle assembly of FIG. 1 in a capped position following use with the needle in a locked state.

With reference now to FIG. 5, the needle assembly 100 is shown in a locked state with the needle 104 positioned on the second side 138 of the latch 128, such as by pivoting the cap 110 from the retracted position shown in FIG. 4A in the reverse direction to capture the needle 104 within the sidewalls 114a, 114b of the cap 110. The needle assembly 100 is shown without the syringe 230, which can be present while pivoting the cap 110 to the locked or capped position. During the rotation and prior to locking the needle 104 below the ramp 134 shown in FIG. 5, the needle 104 contacts or impacts the top 133 of the ramp 134 at a central section of the wall between the two ends 240a, 240b as the cap 110 is rotated over the needle. As the wall 134 is orientated in the direction of rotation of the cap, the needle slides down the ramp 134 and the needle 104, the leg 132, or both the needle and the leg deflect to clear one another. Once the needle 104 clears the lower edge 240a of the ramp 134, it snaps back under the ramp 134 and is trapped by the ramp and the leg, which define a lock space 242 having an acute angle. Once in the position shown on the second side 138 of the latch 128, the needle is secured by the acute angle defining the lock space 242.

Thus, the present needle assembly 100 is understood to comprise a cap hinged to a base unit by a flexible hinge, which together defines a packaged housing. The needle assembly further comprises a needle hub having a needle and wherein the needle hub is unitarily formed with the base unit. In an alternative embodiment, the needle hub is engaged to a C-type clamp located on the base unit and the flexible hinge is a thermoplastic film adhered to both the cap and the base unit. The thermoplastic film has a length that spans across a seam or interface between the cap and the base unit. The needle assembly 100 has a packaged state (FIG. 3) in which a film cover 190 is affixed to an open perimeter edge of the package housing 156, which seals the needle hub 102 and needle 104 within the interior cavities 118, 146 of the cap and the base unit. In the packaged state, the needle 104 is held in a temporary hold position on the first side 136 of a latch 128 located inside the cavity of the cap. The cap is retractable away from the needle to expose the needle for an injection or for taking a sample. The needle hub is usable with a standardized Luer tip, such as a syringe tip. After use, the needle may be capped by pivoting the cap over the needle and latching the needle against the latch by moving the needle past a ramp over to a lock side of the latch, which has an acute angle formed between a leg and the slanted wall. In one example, the film cover is affixed to a length of the package housing and the width of the packaged housing. The film cover is removable from the length and the width of the package housing to allow access to the needle and needle hub located inside the walls of the cap and of the base unit, respectively.

Figure 6:
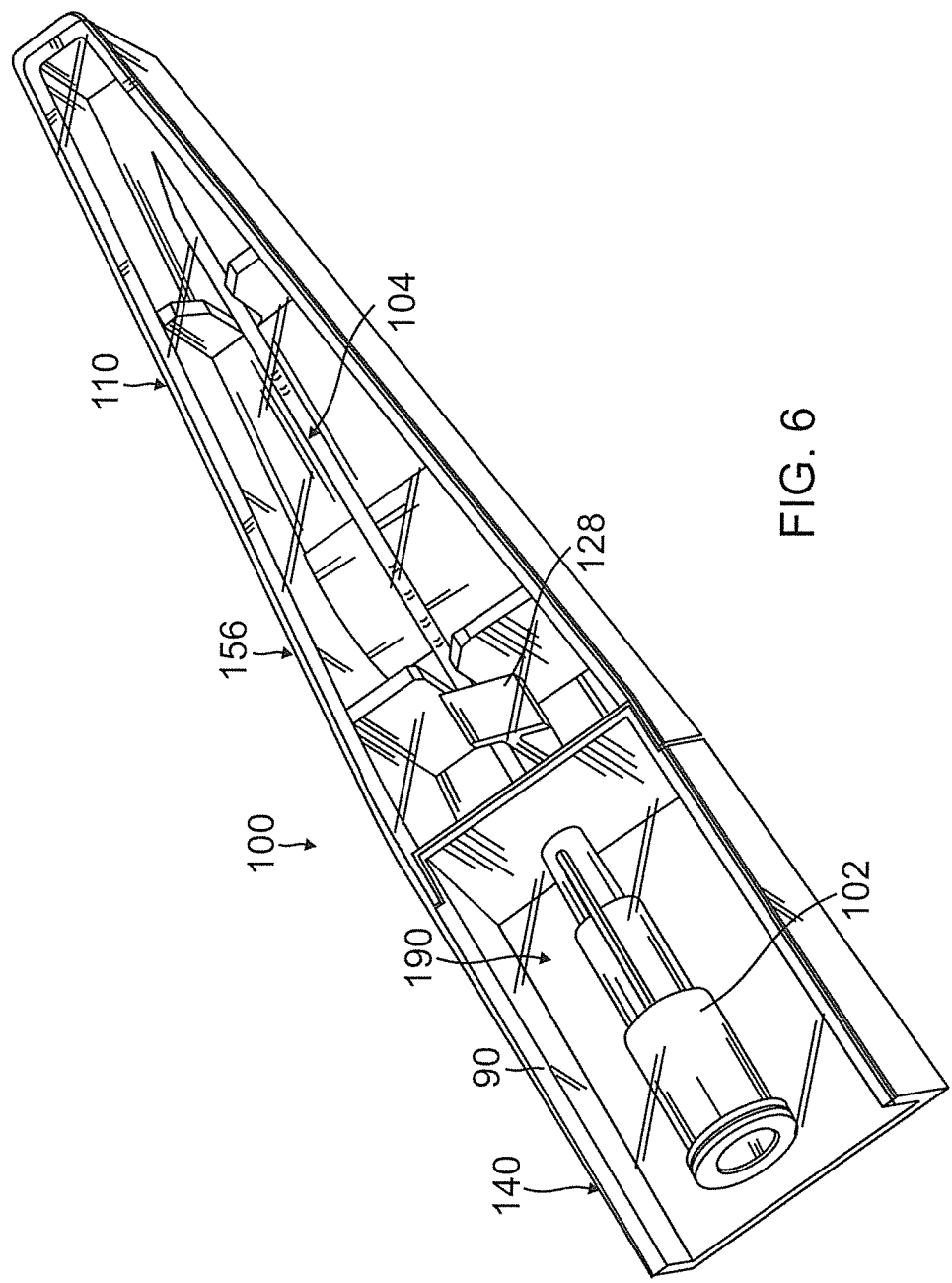
FIG. 6 shows the needle assembly of FIG. 3 in perspective view.

FIG. 6 is a perspective view of the needle assembly 100 of FIG. 3 with a transparent film layer 190. In other examples, the film layer can be opaque or semi-opaque and can have printed information on the film, such as product information. The transparent film allows the cap 110, base unit 140, needle 104, needle hub 102, and latch 128 to be more clearly viewed even when the film layer 190 is attached to the open perimeter edge 90 of the packaged housing 156.

Figure 7:
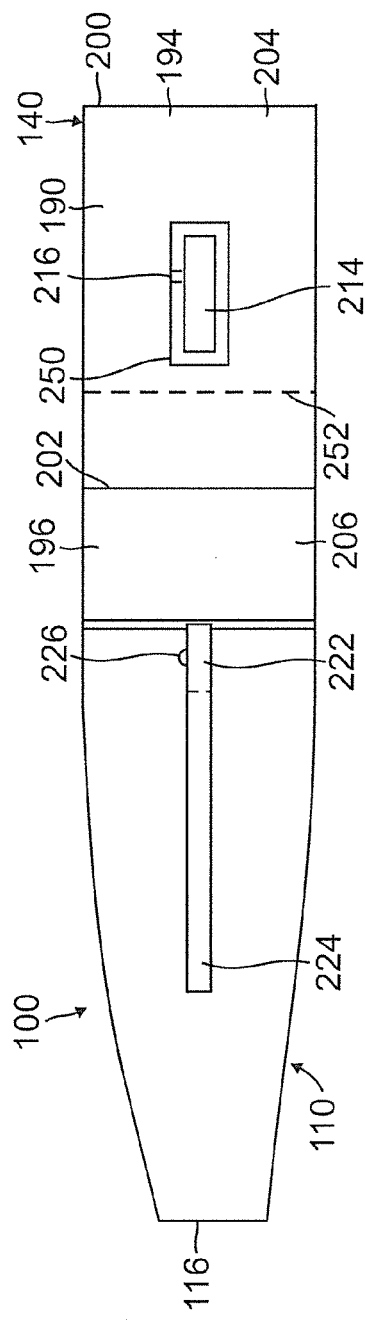
FIG. 7 shows a top view of the cap and the base unit of the needle assembly of FIG. 1.

FIG. 7 is a top view of the rear or back side of the needle assembly 100 of FIG. 1, which shows the rear exterior surface 194 of the base unit 140 and the rear exterior surface 196 of the cap 110, along with the seam 202 located between the two. Also shown is the recess 214 for receiving the tab 222 on the cap 110 to hold the cap in the retracted position to expose the needle tip. Also shown is a cut-out 250 on the film cover 190 around the recess 214 to facilitate engagement between the first and second detent members 216, 226. As previously discussed, a perforation instead of a cut-out may be provided around the recess 214. Also shown is a perforation 252 on the rear exterior surface 194 of the base unit 140, which is an alternative embodiment to the film cover layer 190 having a separation line at the first base corner 199, the second base corner 200 or somewhere on the rear exterior surface 194 of the base unit. As shown, the first film piece 204 of the film cover layer 190 extends from the end wall 116 of the cap past the first base corner 199, and past the second base corner 200 and extends to the perforation 252. Said differently, this first film piece 204 may be removed from the end wall 116 of the cap all the way to the perforation 252. For this version of the first film piece 204, the cut-out 250 around the recess 214 may be omitted, i.e., providing a solid film section around the recess, since the entire recess will be exposed upon removable of the first film piece. The second film piece 206 shown will remain with the cap 110 and the base unit 140 and functions as a flexible hinge between the two components. In an alternative embodiment, a living hinge is provided between the cap 110 and the base unit 140.

Figure 9:
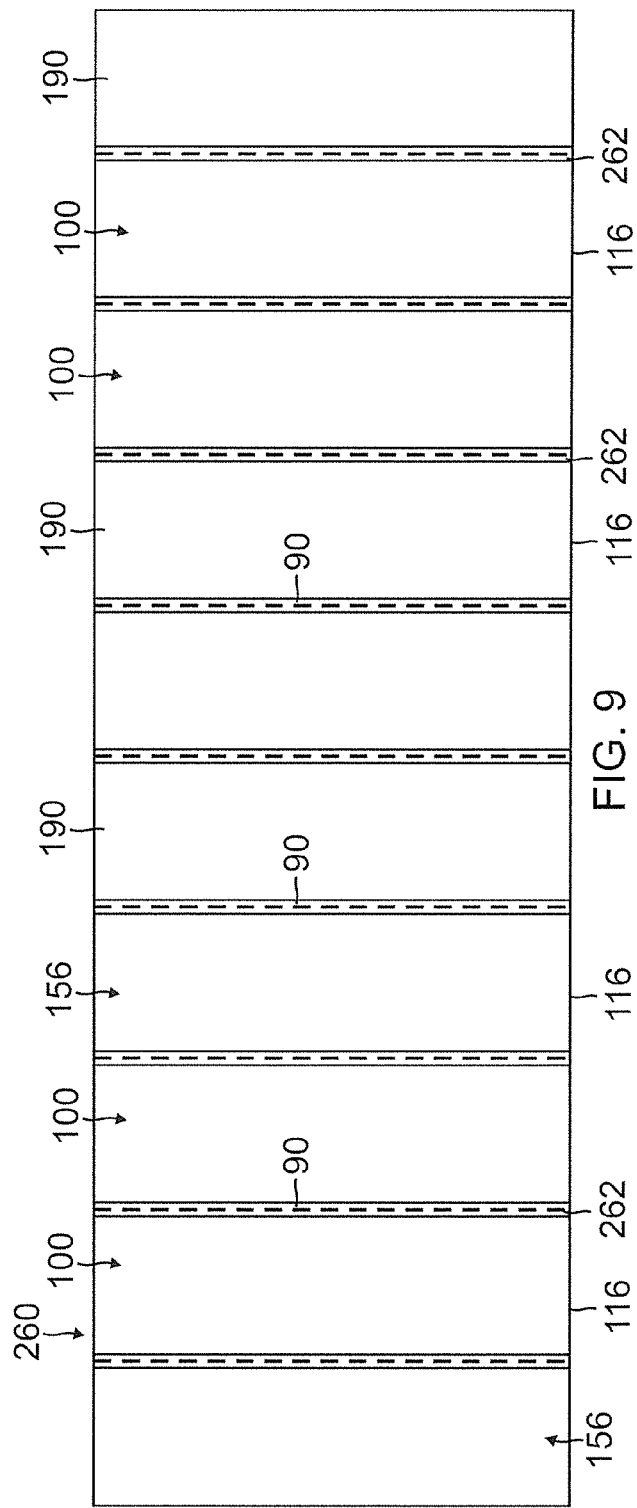
FIG. 9 shows an array of needle assemblies joined to one another with adjacent needle assemblies separated by a tear line.

FIG. 9 is a schematic top view of a plurality of needle assemblies 100 in an array 260. As shown, a needle assembly 100 is joined to one or two adjacent needle assemblies along a tear line 262, which can be a perforation formed on the film cover layer 190 between two adjacent side walls 114a/114b, 144a/144b of the cap 110 and base unit 140 of two adjacent needle assemblies 100. The array 260 is preferred when the needle assemblies 100 are provided to end users in bulk. As shown, each needle assembly 100 is generally rectangular in shape. In an array embodiment, the cap 110 of each needle assembly 100 may be provided with a general rectangular shape to provide for a uniform array. In other embodiments, the package housing 156 of each needle assembly 100 can have different shapes and the seam corresponding to the tear line 262 does not have to extend the entire length of two adjacent needle assemblies.

In use, a needle assembly 100 may be separated from the array 260 one at a time along the tear line 262. Once a single needle assembly 100 is separated from the array 260, the film cover layer 190 of each needle assembly 100 may be removed and the needle assembly used in the manner described above.

Figure 8:
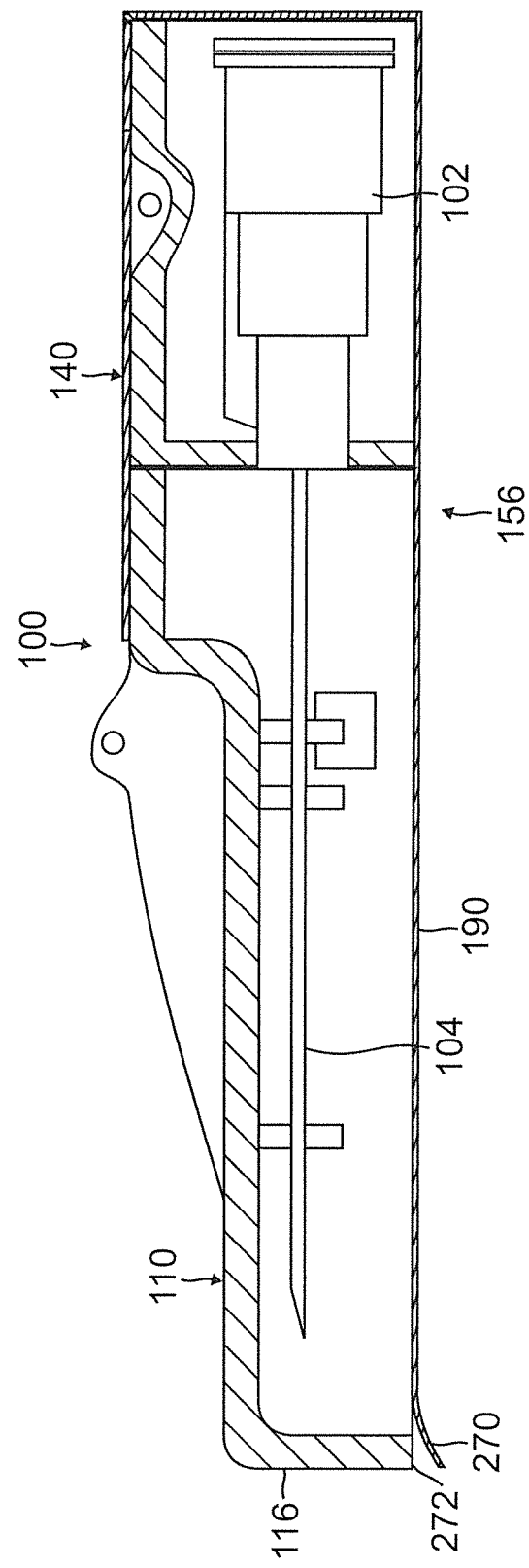
FIG. 8 shows the needle assembly of FIG. 3 with the film cover partially removed.

FIG. 8 is a schematic cross-sectional side view of the needle assembly 100 of FIG. 3, which shows the film cover layer 190 partially opened near the end wall 116 of the cap 110. The film layer 190 may be provided with an extended pull tab 270, which extends beyond the end edge 272 of end wall 116. The pull tab 270 presents a convenient point or location to grab and pull on the film cover 190 to remove it from the package housing 156. As described above, the film cover 190 may be wider at the distal end area of the cap so that pull tabs are provided on either side of end wall 116.

FIG. 10 is a schematic cross-section end view of a dispensing system 280 comprising a dispenser 282 and an array 260 of needle assemblies 100, which may be one of the needle assemblies discussed elsewhere herein. As shown, the dispenser 282 comprises a frame 284 for placing the dispenser system on a counter top, table top, trolly, or for mounting the dispenser system on a wall. A shell 285 is provided for holding the array of needle assemblies within the dispenser 282. The dispenser 282 may be hung on a wall using one or more screws passing through the wall surface of the frame 284 or resting the lower frame section 283 on a table top. The shell 285 comprises a storage area 286 for holding the plurality of needle assemblies. The storage area 286 is bounded by a panel system 288 that can be operated to open or close access to the storage area 286. In one example, the panel system 288 comprises a door 290 that can pivot about a hinge 292. In another example, a side wall can snap on and off to provide access for loading a roll of needles into the dispenser. The shell 285 further comprises a dispenser opening 294 locating adjacent a frame extension 296 for dispensing the needle assemblies 100, which has a lip 314 to prevent the needle assemblies from spilling over the edge. The dispenser may be made from metal or from plastic.

As shown, the needle assemblies 100 are provided as an interconnected array 260, similar to that shown in FIG. 9. The array 260 is rolled into a rolled bundle of needle assemblies and placed into the storage space 286 of the dispenser system. In practice, the end-most needle assembly 298 is placed through the dispenser opening 294 and rested on the frame extension 296 before the remaining rolled bundle of needle assemblies are lowered into the storage space 286. Each needle assembly 100 may be used by a user by grabbing the end-most needle assembly 298 and separating it at the tear line 262. Once separated, the needle assembly may be used as described above.

Figure 11:
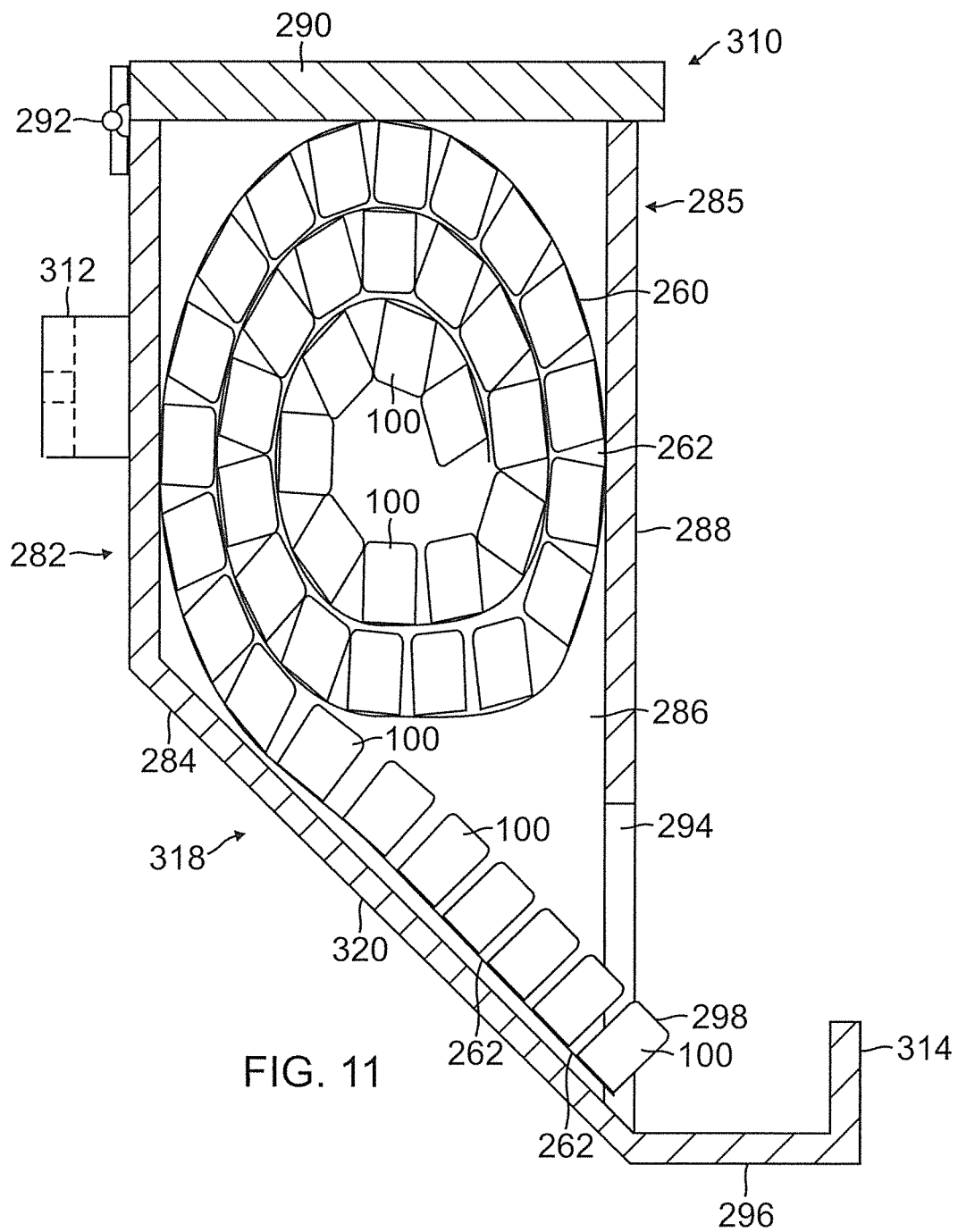
FIG. 11 shows an alternative dispenser system in accordance with aspects of the present disclosure for dispensing needle assemblies.

FIG. 11 is a schematic cross-section end view of an alternative dispensing system 310 comprising dispenser 282 and an array 260 of needle assemblies 100, which may be one of the needle assemblies discussed elsewhere herein. The dispenser comprises a frame 284 for mounting the dispenser system on a wall. A mounting bracket 312 is provided and attaches to the frame 284. The mounting bracket 312 may be hung on a wall first and then the frame 284 attached to the mounting bracket 312. A shell 285 for holding the array of needle assemblies is provided with the frame 284. The shell 285 comprises a storage area 286 for holding the plurality of needle assemblies 100. The storage area 286 is bounded by a panel system or wall structure 288 having a lid or door 290 that can be operated to open or close access to the storage area 286. In one example, the door 290 is located along an upper region of the dispenser and is pivotably mounted to the shell via a hinge 292. The shell 285 further comprises a dispenser opening 294 located adjacent a frame extension 296 for dispensing the needle assemblies 100. The frame extension 296 has a lip 314 to act as a stop to prevent the needle assemblies from spilling over the frame extension 296.

As shown, the needle assemblies 100 are provided as an interconnected array 260, similar to that shown in FIG. 9. The array 260 is rolled into a rolled bundle of needle assemblies and placed into the storage space 286 of the dispenser system. In practice, the end-most needle assembly 298 is placed through the dispenser opening 294 and rested on the frame extension 296 before the remaining rolled bundle of needle assemblies are lowered into the storage space 286. Each needle assembly 100 may be used by a user by simply grabbing the end-most needle assembly 298 and separating it at the tear line 262. Once separated, the needle assembly may be used as described above.

To ensure adequate or proper loading of the needle assemblies 100 at the dispenser opening 294, the present dispenser 280 incorporates a hopper style lower end section 318. As shown, the lower end section 318 is provided with a slanted bottom wall 320 to increase the distance or gap between the end-most needle assembly 298 and the rolled section 322 of the array 260 of needle assemblies. This gap ensures a sufficient head pressure due to gravity on the end-most needle assembly 298 to ensure that it will slide down the sloped bottom wall 320 and be available at the opening 294 for use.

In an alternative embodiment, a plurality of needle assemblies 100 are positioned inside the storage space of the dispenser system of FIGS. 10 and/or 11 as a dispersed bundle, i.e., without a tear line connecting two adjacent needle assemblies. In still other embodiments, the needle assemblies are positioned inside the storage space as a dispersed bundle and in an array.

Although limited embodiments of needle assemblies and their components including dispensing system have been specifically described and illustrated herein, many modifications and variations will be apparent to those skilled in the art. Accordingly, it is to be understood that the needle assemblies and their components constructed according to principles of the disclosed device, system, and method may be embodied other than as specifically described herein. The disclosure is also defined in the following claims.

What is claimed is:

1. A combination safety needle assembly and a packaging system for the safety needle assembly comprising:
    a base unit comprising a base wall located between two sidewalls and defining an interior cavity;
    a cap connected to the base unit at an interface, the cap comprising a base wall located between two sidewalls of the cap and defining an interior cavity having a latch;
    a needle hub and a needle combination, said needle hub attached to the base unit and said needle extending into the interior cavity of the cap;
    wherein the sidewalls of the cap and the sidewalls of the base unit define an open perimeter edge and the interior cavity of the cap and the interior cavity of the base unit define a package cavity; and
    wherein a thermoplastic film is attached to the open perimeter edge and extends across the interface between the cap and the base unit to enclose the combination needle hub and needle within the package cavity and forms a hinge at the interface to allow the cap to pivot relative to the base unit along the hinge.

2. The combination of claim 1, wherein the thermoplastic film comprises a first film piece and a second film piece separated from one another by a perforation or a distinct separation.

3. The combination of claim 1, wherein the two sidewalls of the base unit and the two sidewalls of the cap overlap along an axial direction when the cap is closed over the needle.

4. The combination of claim 1, wherein the needle hub is unitarily formed with the base unit.

5. The combination of claim 4, wherein the needle hub is molded with a distal wall on the base unit.

6. The combination of claim 5, wherein the distal wall on the base unit connects to the base wall and the two sidewalls of the base unit.

7. The combination of claim 1, wherein the latch comprises a post and a ramp mounted at an end of the post.

8. A combination safety needle assembly and a packaging system for the safety needle assembly comprising:
    a base unit comprising an enclosure having a base wall located between two sidewalls, said enclosure having an interior cavity, a perimeter edge with a proximal end edge, and an exterior surface on the base wall of said base unit;
    a cap hingedly connected to the base unit at an interface by a film layer, the cap comprising an enclosure having a base wall located between two sidewalls of the cap, said enclosure defining an interior cavity having a latch and a perimeter edge and said base wall of said cap having an exterior surface;
    a needle hub and a needle combination, said needle hub attached to the base unit and said needle extending into the interior cavity of the cap;
    wherein the needle hub is recessed within the proximal end edge of the base unit and wherein a film cover is attached to the perimeter edge of the cap, the perimeter edge of the base unit, and the proximal end edge of the base unit to enclose the combination needle hub and needle within the interior cavity of the cap and the interior cavity of the base unit; and
    wherein said film layer that connects said cap to said base unit comprises an exposed terminal end and extends over at least part of the exterior surface of the base unit and at least part of the exterior surface of the cap.

9. The combination of claim 8, wherein the film layer and the film cover are spaced from one another.

10. The combination of claim 8, wherein a perforation is located between the film layer and the film cover.

11. The combination of claim 8, wherein each sidewall of the cap comprises a proximal end edge and each sidewall of the base unit comprises a distal end edge and wherein the two proximal end edges of the cap project proximally of the two distal end edges of the base unit such that the two sidewalls of the cap and the two sidewalls of the base unit overlap at least in part along an axial direction when the cap is closed over the needle.

12. The combination of claim 8, wherein the needle safety assembly is a first needle safety assembly and further comprising a second needle safety assembly connected to the first needle safety assembly and has a tear line located therebetween.

13. The combination of claim 8, wherein the needle hub is unitarily formed with the base unit.

14. The combination of claim 8, wherein the needle hub snap fits into a C-clamp formed on the base unit.

15. A dual use needle assembly comprising a packaging housing having a needle hub and a needle located within an enclosure having a perimeter edge and a film cover attached to the perimeter edge to seal the needle hub and the needle within the packaging housing, and wherein the packaging housing comprises a cap having two sidewalls and two end edges and a base unit having two sidewalls and two end edges, and wherein an isolation zone is defined by the sidewalls of the cap and the sidewalls of the base unit overlapping along an axial direction when the cap is closed over the needle such that the two end edges of the base unit extends distally of the two end edges of the cap and the two end edges of the cap extends proximally of the two end edges of the base unit at the isolation zone.

16. The dual use needle assembly of claim 15, wherein the cap is attached to the base unit by a living hinge.

17. The dual use needle assembly of claim 15, wherein the cap is attached to the base unit by a second film cover that spans across a seam located between the cap and the base unit at the isolation zone.

18. The dual use needle assembly of claim 15, further comprising a second dual use needle assembly and a third dual use needle assembly connected in an array.

19. A method for manufacturing a dual use needle assembly comprising:
forming a base unit comprising two sidewalls with outer edges, a base wall located between the two sidewalls, and a needle hub having a needle with a sharpened needle tip;
forming a cap comprising two sidewalls with outer edges and a base wall located between the two sidewalls;
attaching a film cover to the outer edges of the two sidewalls of the cap and of the base unit to enclose the needle and the needle hub within an interior cavity; and
forming an isolation zone by overlapping the two sidewalls of the cap with the two sidewalls of the base unit along an axial direction when the cap is closed over the needle such that two end edges of the base unit extends distally of two end edges of the cap and the two end edges of the cap extends proximally of the two end edges of the base unit at the isolation zone.

20. The method of claim 19, wherein the film cover has a gap or a perforation along a length thereof.

21. The method of claim 19, wherein the base unit and the needle hub are unitarily formed.

22. The method of claim 19, further comprising placing the needle on a first side of a latch comprising a post and a ramp.

23. A dispenser system comprising a dispenser having a wall structure defining a storage space, (1) an array of needle assemblies, (2) a dispersed bundle of needle assemblies, or (3) a combination of an array of needle assemblies and a dispersed bundle of needle assemblies located in the storage space; and wherein each needle assembly comprises:
a package housing comprising a base unit comprising sidewalls and a base wall hingedly connected to a cap comprising sidewalls and a base wall;
a film cover affixed to a perimeter edge of the package housing;
a needle hub and needle sealed inside the package housing by the film cover;
sidewalls of the cap and the base unit overlapping along an axial direction when the cap is closed over the needle;
wherein the film cover extends across an interface between the cap and the base unit to form a hinge at the interface to allow the cap to pivot relative to the base unit along the hinge; and
wherein the film cover located at the interface and the film cover affixed to the perimeter edge of the packaging housing are spaced from one another or has a perforation therebetween.

24. The combination of claim 7, wherein the ramp and the post define an obtuse angle on a first side and an acute angle on a second side and wherein the needle is located on the first side in a holding state and on the second side in a locked state.

25. A dispenser system comprising a dispenser having a wall structure defining a storage space, (1) an array of needle assemblies, (2) a dispersed bundle of needle assemblies, or (3) a combination of an array of needle assemblies and a dispersed bundle of needle assemblies located in the storage space; and wherein each needle assembly comprises:
a package housing comprising a base unit comprising sidewalls and a base wall hingedly connected to a cap comprising sidewalls and a base wall;
a film cover affixed to a perimeter edge of the package housing;
a needle hub and needle sealed inside the package housing by the film cover;
sidewalls of the cap and the base unit overlapping along an axial direction when the cap is closed over the needle;
an isolation zone by overlapping the two sidewalls of the cap with the two sidewalls of the base unit along an axial direction when the cap is closed over the needle such that two end edges of the base unit extends distally of two end edges of the cap and the two end edges of the cap extends proximally of the two end edges of the base unit at the isolation zone; and
wherein the film cover extends across an interface between the cap and the base unit to form a hinge at the interface to allow the cap to pivot relative to the base unit along the hinge.

26. The combination of claim 8, wherein the proximal end edge of the of the base unit is generally orthogonal to the needle.

27. The dual use needle assembly of claim 16, wherein the base unit comprises a second set of two end edges at a proximal end and wherein the film cover is attached to the second set of two end edges.

28. The dual use needle assembly of claim 17, wherein the film cover extends over at least part of an exterior surface of the base unit and an exterior surface of the cap and comprises an exposed terminal end.

* * * * *

UNITED STATES PATENT AND TRADEMARK OFFICE
CERTIFICATE OF CORRECTION

Page 1 of 1

PATENT NO. : 9,867,951 B2
APPLICATION NO. : 14/248004
DATED : January 16, 2018
INVENTOR(S) : Kevin Woehr It is certified that error appears in the above-identified patent and that said Letters Patent is hereby corrected as shown below:

In the Specification

In Column 1, Line 25, delete "removeable" and insert -- removable --, therefor.

In the Claims

In Column 16, Line 36, in Claim 26, delete "of the of the" insert -- of the --, therefor.

Signed and Sealed this
Nineteenth Day of November, 2019

Andrei Iancu
*Director of the United States Patent and Trademark Office*